(12) United States Patent
    Dzuricky et al.

(10) Patent No.: US 12,636,456 B2
(45) Date of Patent: May 26, 2026

(54) EXHAUST DIFFUSER ARRANGEMENT AND CPAP MASK INCLUDING SAME

(71) Applicant: KONINKLIJKE PHILIPS N.V., Eindhoven (NL)

(72) Inventors: Anna Dzuricky, Erie, PA (US); Alexander Enzman, Pittsburgh, PA (US); Lauren Patricia Chodkowski, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 550 days.

(21) Appl. No.: 18/208,234

(22) Filed: Jun. 9, 2023

(65) Prior Publication Data

US 2023/0398320 A1      Dec. 14, 2023

Related U.S. Application Data

(60) Provisional application No. 63/351,027, filed on Jun. 10, 2022.

(51) Int. Cl.
    *A61M 16/06*      (2006.01)
    *A61M 16/08*      (2006.01)
(52) U.S. Cl.
    CPC .... *A61M 16/0666* (2013.01); *A61M 16/0816* (2013.01); *A61M 16/0875* (2013.01)
(58) Field of Classification Search
    CPC .......... A61M 16/0666; A61M 16/0816; A61M 16/0875; A61M 16/06; A61M 2205/0216; A61M 16/0683; A61M 2205/42
    See application file for complete search history.

(56) References Cited

U.S. PATENT DOCUMENTS 5,438,981 A      8/1995  Starr
6,561,191 B1 *   5/2003  Kwok .................... A62B 18/10
                                                 128/205.24
(Continued)

FOREIGN PATENT DOCUMENTS

EP        2022528 A2      2/2009
EP        2027880 A1      2/2009
(Continued)

OTHER PUBLICATIONS

Testing, testing.

*Primary Examiner* — Victoria Murphy
(74) *Attorney, Agent, or Firm* — Michael W. Haas

(57)      ABSTRACT

An exhaust diffuser arrangement includes: a housing; a cavity defined within the housing, the cavity being sized and configured to house a diffuser element therein; an inlet defined in the housing, the inlet structured to communicate gases from a main cavity to the diffuser cavity; and an outlet defined in the housing, the outlet structured to communicate gases from the diffuser cavity to an exterior environment. The housing is formed from an elastic material adjacent the outlet such that the housing, and thus the outlet, is elastically deformable from: a first sizing wherein the outlet is structured to prohibit the diffuser element from passing therethrough and thus the diffuser element is captively positioned within the cavity; and a second sizing in which the outlet is structured to allow the diffuser element to readily pass through the outlet for placing the diffuser element in or from the cavity.

15 Claims, 9 Drawing Sheets

(56)                    References Cited

U.S. PATENT DOCUMENTS

| | | | | |
|---|---|---|---|---|
| 6,581,594 B1 * | 6/2003 | Drew | ................ | A61M 16/0633 |
| | | | | 128/207.12 |
| 6,662,803 B2 * | 12/2003 | Gradon | ............ | A61M 16/0069 |
| | | | | 128/206.16 |
| 7,559,326 B2 * | 7/2009 | Smith | ................ | A61M 16/208 |
| | | | | 128/205.24 |
| 2006/0196509 A1 * | 9/2006 | Drew | ................ | A61M 16/0633 |
| | | | | 128/206.21 |
| 2013/0213400 A1 | 8/2013 | Barlow | | |
| 2014/0044905 A1 | 2/2014 | Nickol | | |
| 2019/0262568 A1 * | 8/2019 | Chow | .................. | A61M 16/06 |
| 2020/0129724 A1 | 4/2020 | Nelson | | |
| 2021/0113788 A1 | 4/2021 | Huddart | | |
| 2021/0128861 A1 | 5/2021 | McAuley | | |
| 2021/0379325 A1 | 12/2021 | Dantanarayana | | |
| 2022/0023572 A1 | 1/2022 | Henry | | |
| 2022/0040431 A1 * | 2/2022 | Chow | ............... | A61M 16/0627 |

FOREIGN PATENT DOCUMENTS

| | | | | | |
|---|---|---|---|---|---|
| EP | 3202449 | A1 | 8/2017 | | |
| WO | WOL2018126295 | A1 | 7/2018 | | |
| WO | WO2020170207 | A1 | 8/2020 | | |
| WO | WO2020208523 | A1 | 10/2020 | | |
| WO | WO2021012005 | A1 | 1/2021 | | |
| WO | WO-2022073075 | A1 * | 4/2022 | ........ | A61M 16/0683 |

* cited by examiner

Pressure Generating Device

EXHAUST DIFFUSER ARRANGEMENT AND CPAP MASK INCLUDING SAME

CROSS-REFERENCE TO RELATED APPLICATIONS

This patent application claims the priority benefit under 35 U.S.C. § 119(e) of U.S. Provisional Application No. 62/351,027, filed on Jun. 10, 2022, the contents of which are herein incorporated by reference.

BACKGROUND OF THE INVENTION

1. Field of the Invention

The present invention pertains to patient interface devices for use in delivering a pressurized flow of a treatment gas to the airway of a patient and, more particularly, to exhaust port arrangements for use therein.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient, so that a flow of breathing gas can be delivered from a pressure/flow generating device to the airway of the patient. It is known to maintain such devices on the face of a wearer by a headgear having one or more straps adapted to fit over/around the patient's head. Because such patient interface devices are typically worn for an extended period of time, it is important for the headgear to maintain the mask component of the device in a tight enough seal against the patient's face without discomfort.

Conventional CPAP masks, commonly utilize exhalation arrangements found in the front of a faceplate or in an elbow connected to the faceplate. Such arrangements use a single exhaust port or a series of exhaust ports that release jets of air. Such jet or jets of air are often directed toward the user's bedpartner, which causes discomfort and irritation. Additionally, such jet(s) produce(s) a white noise, which can also be disruptive. Some CPAP systems attempt to address such issues by mounting a diffuser element on the outside of the mask over the exhaust port. However, such solutions are often rigid and bulky and thus negatively affect the comfort of the mask. Additionally, traditional diffuser elements become waterlogged from moisture (from exhaled gases and/or humidified treatment gases) from gases passing therethrough. Once waterlogged, the diffuser element becomes an obstruction that no longer serves to muffle the noise or diffuse the jet of exhaled gas but instead becomes an obstruction that prevents passage of gases through the exhaust port(s), thus rendering them generally inoperable. There is therefore a need to provide improved exhaust arrangements for use with CPAP masks.

SUMMARY OF THE INVENTION

As a first aspect of the present invention, an exhaust diffuser arrangement for exhausting gases from a main cavity of a patient interface used in providing a flow of a breathing gas to the airway of a patient is provided. The exhaust diffuser arrangement comprises: a diffuser housing; a diffuser cavity defined within the diffuser housing, the diffuser cavity being sized and configured to house a diffuser element therein; a diffuser inlet defined in the housing, the diffuser inlet structured to communicate gases from the main cavity to the diffuser cavity; and a diffuser outlet defined in the housing, the diffuser outlet structured to communicate gases from the diffuser cavity to an exterior environment to the patient interface. The diffuser housing is formed from an elastic material adjacent the diffuser outlet such that the diffuser housing, and thus the diffuser outlet, is elastically deformable from: a first sizing wherein the diffuser outlet is structured to prohibit the diffuser element from passing therethrough and thus the diffuser element is captively positioned within the diffuser cavity, and a second sizing in which the diffuser outlet is structured to allow the diffuser element to readily pass through the diffuser outlet for placing the diffuser element in, or removing the diffuser element from, the diffuser cavity.

The exhaust diffuser arrangement may further comprise a number of protrusions extending into the diffuser cavity from the diffuser housing, wherein each protrusion of the number of protrusions is structured to space the diffuser element from a corresponding portion of the diffuser housing to form a non-linear pathway between the diffuser element and the diffuser housing that extends from the diffuser inlet to the diffuser outlet.

The exhaust diffuser arrangement may further comprise a number of ribs extending into the diffuser cavity from the diffuser housing, wherein each rib of the number of ribs is structured to space the diffuser element from a corresponding portion of the diffuser housing to form a non-linear pathway between the diffuser element and the diffuser housing that extends from the diffuser inlet to the diffuser outlet.

The exhaust diffuser arrangement may further comprise the diffuser element captively positioned within the diffuser cavity. The diffuser element may be a piece of absorbent material.

As another aspect of the present invention, a patient interface for use in providing a flow of a breathing gas to the airway of a patient is provided. The patient interface comprises: a sealing arrangement structured to sealingly engage about an airway of the patient; a body; a main cavity defined within the body, the main cavity being structured to receive the flow of breathing gas; a patient aperture surrounded by the sealing arrangement, the patient aperture structured to convey the flow of breathing gas from the main cavity to the airway of the patient; and an exhaust diffuser arrangement such as previously described.

As yet a further aspect of the present invention, an arrangement for providing a flow of treatment gas to the airway of a patient is provided. The arrangement comprises: a tubing assembly comprising a manifold portion and a number of tubular portions, each tubular portion extending from the manifold portion to a distal end, the manifold portion being structured to receive the flow of treatment gas and each tubular portion being structured to convey the flow of treatment gas from the manifold portion to the distal end thereof; and a patient interface coupled to the distal end of each tubular portion, the patient interface comprising: a sealing arrangement structured to sealingly engage about an airway of the patient; a body; a main cavity defined within the body, the main cavity being structured to receive the flow of breathing gas from the distal end of each tubular portion; a patient aperture surrounded by the sealing arrangement, the patient aperture structured to convey the flow of breathing gas from the main cavity to the airway of the patient; and an exhaust diffuser arrangement such as previously described.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
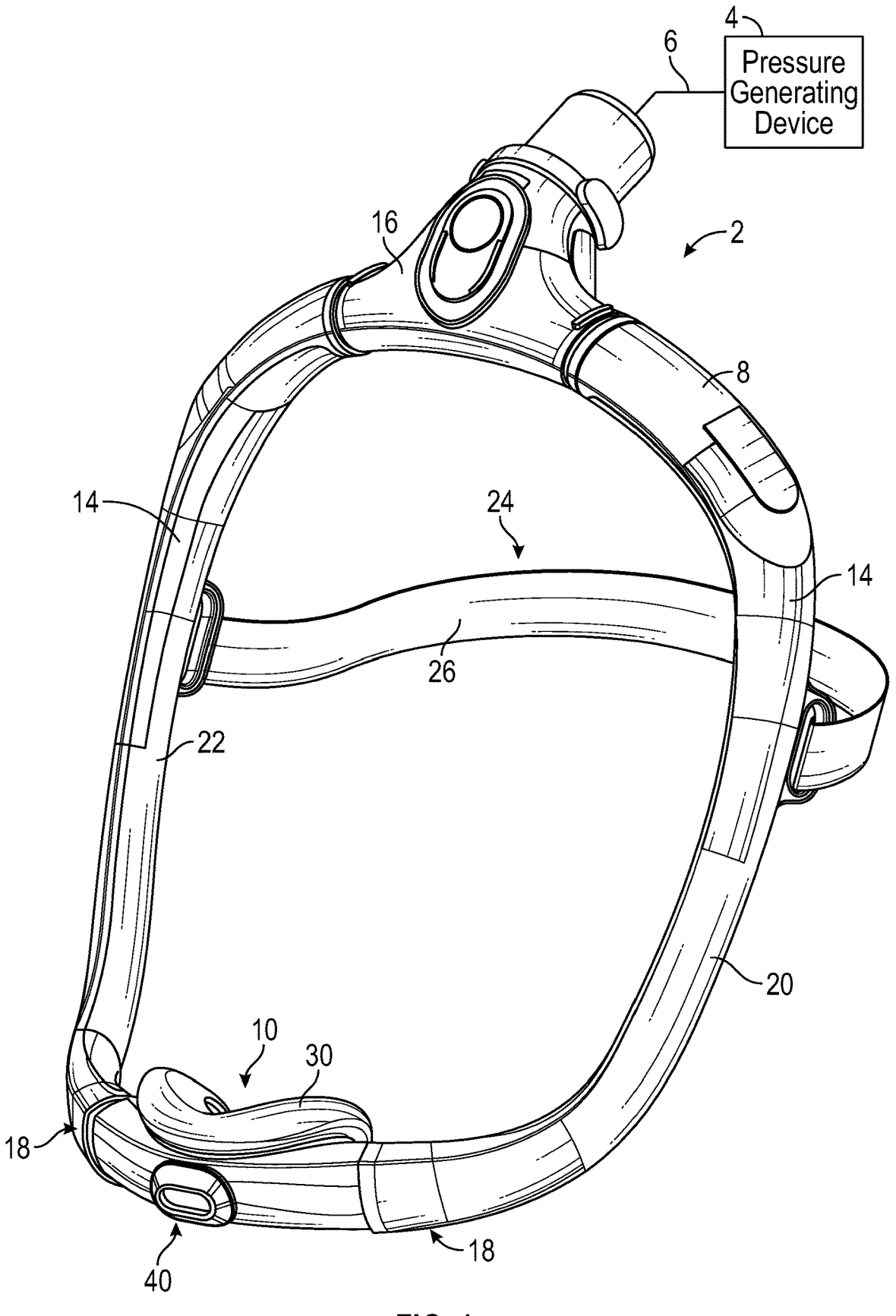
FIG. 1 is a partially schematic view of a respiratory interface system in accordance with an example embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, the statement that two or more parts or components "engage" one another shall means that the parts exert a force against one another either directly or through one or more intermediate parts or components. As used herein, the word "unitary" means a component is created as a single piece or unit. That is, a component that includes pieces that are created separately and then coupled together as a unit is not a "unitary" component or body. As used herein, the term "number" shall mean one or an integer greater than one (i.e., a plurality).

As used herein, a "coupling assembly" includes two or more couplings or coupling components. The components of a coupling or coupling assembly are generally not part of the same element or other component. As such the components of a "coupling assembly" may not be described at the same time in the following description.

As used herein, a "coupling" is one element of a coupling assembly. That is, a coupling assembly includes at least two components, or coupling components, that are structured to be coupled together. It is understood that the elements of a coupling assembly are compatible with each other. For example, in a coupling assembly, if one coupling element is a snap socket, the other coupling element is a snap plug.

As used herein, "correspond" indicates that two structural components are sized and shaped to be similar to each other and may be coupled with a minimum amount of friction. Thus, an opening which "corresponds" to a member is sized slightly larger than the member so that the member may pass through the opening with a minimum amount of friction. This definition is modified if the two components are said to fit "snugly" together or "snuggly correspond." In that situation, the difference between the size of the components is even smaller whereby the amount of friction increases. If the element defining the opening and/or the component inserted into the opening is/are made from a deformable or compressible material, the opening may even be slightly smaller than the component being inserted into the opening. This definition is further modified if the two components are said to "substantially correspond." "Substantially correspond" means that the size of the opening is very close to the size of the element inserted therein. That is, not so close as to cause substantial friction, as with a snug fit, but with more contact and friction than a "corresponding fit," i.e., a "slightly larger" fit.

Referring to FIG. 1, a respiratory interface system 2 for use in providing a regimen of respiratory therapy to a patient (not shown) according to one example embodiment of the present invention is shown. Respiratory interface system 2 includes a pressure generating device 4 (shown schematically), a delivery conduit 6 (shown schematically) fluidly coupled to a tubing assembly 8, and a patient interface 10 fluidly coupled to tubing assembly 8. Pressure generating device 4 is structured to generate a flow of positive pressure breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, PA), and auto-titration pressure support devices. Delivery conduit 6 is structured to communicate the flow of breathing gas from pressure generating device 4 to patient interface device 10 through tubing assembly 8 (the breathing gas enters tubing assembly 8 at the top of the head of a patient when tubing assembly 8 and patient interface device 10 are positioned on the head of the patient). Delivery conduit 6, tubing assembly 8 and patient interface device 10 are often collectively referred to as a patient circuit.

Figure 2:
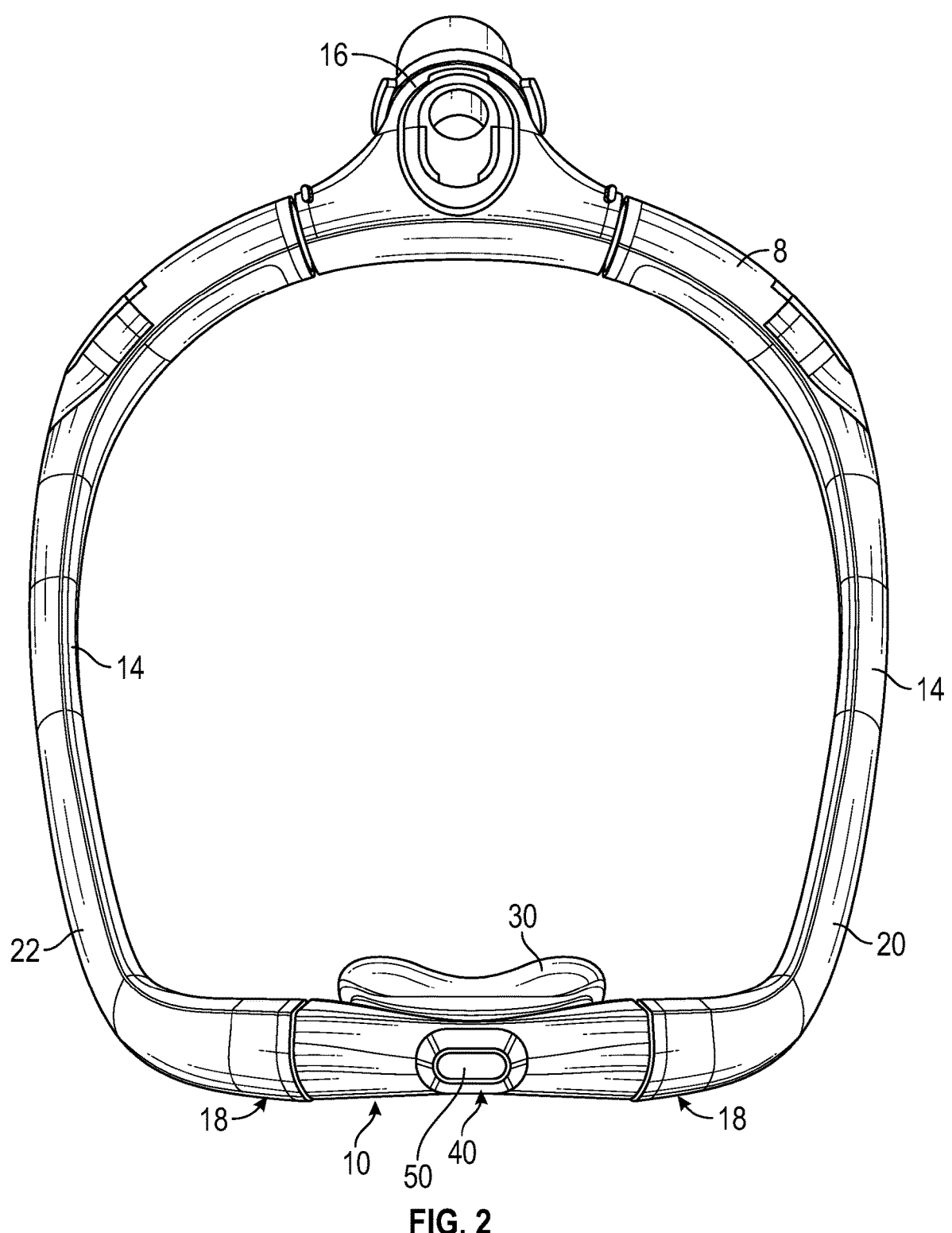
FIG. 2 is a front elevation view of a portion of the respiratory interface system of FIG. 1.
Figure 3:
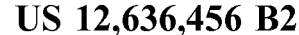
FIG. 3 is a detail view of the front of the patient interface of the system of FIGS. 1 and 2 shown without a diffusion element included in an exhaust arrangement thereof.

Continuing to refer to FIG. 1, and additionally to FIG. 2, tubing assembly 8 includes a number of tubular portions 14 which each extend from a manifold portion 16 to a distal end 18. Distal end 18 of each tubular portion 14 is coupled to, and in fluid communication with, patient interface 10. In example embodiments, tubing assembly 8 is made from plastic and/or silicone and may be formed as a single unitary member or alternately may be formed from a number of separately formed components that are then coupled together via a suitable process. Tubing assembly 8 may also be formed from other suitable materials (e.g., fabric) without varying from the scope of the present invention.

Manifold portion 16 is structured to be coupled to delivery conduit 6, such as via an elbow or other suitable coupling member. When tubing assembly 8 is disposed on the head of a patient, manifold portion 16 is disposed generally at the top of the head of the patient and tubular portions 14 extend generally downward from manifold portion 16 to patient interface device 10. In the example embodiment illustrated in FIGS. 1 and 2, there are two tubular portions 14, namely left and right-side arms 20, 22, which each have a generally non-circular cross-section. That is, each tubular portion 14 is not substantially circular. In another example embodiment, not shown, tubing assembly 8 includes a single tubular portion 14 that extends centrally, i.e., from manifold portion 16 generally over the patient's forehead and nose, to patient interface 10.

In an example embodiment, each tubular portion 14 has a generally D-shaped cross-section wherein the generally flat side of the D-shape is disposed adjacent the patient's head while the curved portion faces away from the patient's head. Tubular portions 14, i.e., left and right-side arms 20, 22, encircle, or partially encircle, the head of a patient. Accordingly, it is to be appreciated that tubing assembly 8, as a result of its basic structure and positioning, generally functions not only as a portion of the supply conduit for providing gas to/from patient interface 10, but also generally functions as a frame, securing patient interface 10 to the head of a patient. Further, in order to help secure patient interface device 10 and tubing assembly 8 to the head of a patient, tubing assembly 8 may further include a support assembly 24, which in the example embodiment shown in FIG. 1 is a strap member 26 coupled to left and right-side arms 20, 22 which partially encircles, the head of a patient. That is, strap member 26 is structured to engage the rear of the head of a patient, and in one example embodiment is structured to fit generally just below the occipital bone of a patient.

Continuing to refer to FIGS. 1 and 2, and additionally to FIGS. 3-6, patient interface 10 includes a sealing arrangement 30 that is structured to seal generally about an airway of a patient. In an exemplary embodiment, such as illustrated in FIGS. 1-6, sealing arrangement 30 is a nasal cushion made of a soft, flexible material, such as, without limitation, silicone, an appropriately soft thermoplastic elastomer, a closed-cell foam, or any other suitable material or combination of such materials. It is to be appreciated, however, that any type of sealing arrangement, such as a nasal/oral mask, a nasal pillow or a full face mask, which facilitates the delivery of the flow of breathing gas to the airway of a patient, may be used as sealing arrangement 30 while remaining within the scope of the present invention. As shown in the sectional view of FIG. 4, sealing arrangement 30 is positioned about, and generally defines, a patient aperture 32 which provides access to a main cavity 34 defined by and within a body 36 of patient interface 10. Main cavity 34 is structured to receive the flow of breathing gas produced by pressure generating device 4 which is then conveyed to the airway of a patient through patient aperture 32. In the example embodiment shown in FIGS. 1-6, main cavity 34 receives the flow of breathing gas produced by pressure generating device 4 via a pair of inlet ports (not numbered) positioned at either end of patient interface 10 that are each coupled to a respective distal end 18 of left and right-side arms 20, 22.

Patient interface 10 further includes an exhaust diffuser arrangement 40 that provides for the exhausting of gases from patient interface 10, and more particularly from main cavity 34 thereof. Referring to FIGS. 3-6, exhaust diffuser arrangement 40 includes a diffuser housing 42, a diffuser cavity 44, a diffuser element 50, a diffuser inlet 46, and a diffuser outlet 48. In an example embodiment, diffuser housing 42 is at least in-part an elastically deformable structure that is mounted onto, or formed integrally as a portion of, housing 36 of patient interface 10. As used herein, an "elastically deformable structure" is a structure that is repeatedly deformable from a first position/shape to a second position/shape upon application of a force or forces that transition and hold the structure in the second position/shape, and that returns to the first position shape upon removal and/or cessation of the force or forces applied thereto. As shown in the sectional views of FIGS. 4 and 6, diffuser cavity 44 is defined by and within diffuser housing 42 such that diffuser element 50 is captively positioned within diffuser cavity 44. Diffuser inlet 46 is defined in diffuser housing 42 and is structured to communicate gases from main cavity 34 of patient interface 10 to diffuser cavity 44. Diffuser outlet 48 is defined in diffuser housing 42 and is structured to communicate gases from diffuser cavity 44 to an exterior environment (e.g., the room in which the patient is receiving a CPAP treatment) to patient interface 10.

Figure 4:
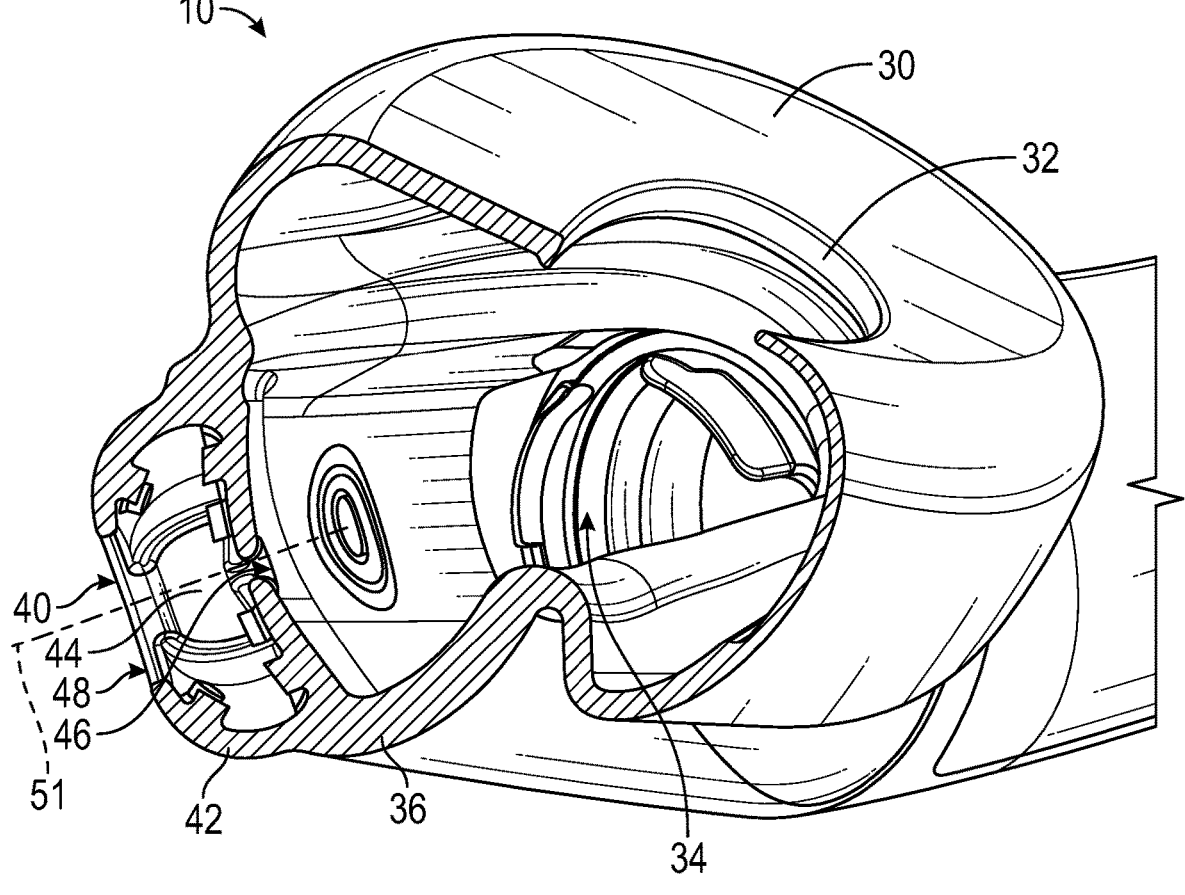
FIG. 4 is a sectional view of the patient interface of FIG. 3 taken along line 4-4 of FIG. 3.
Figure 5:
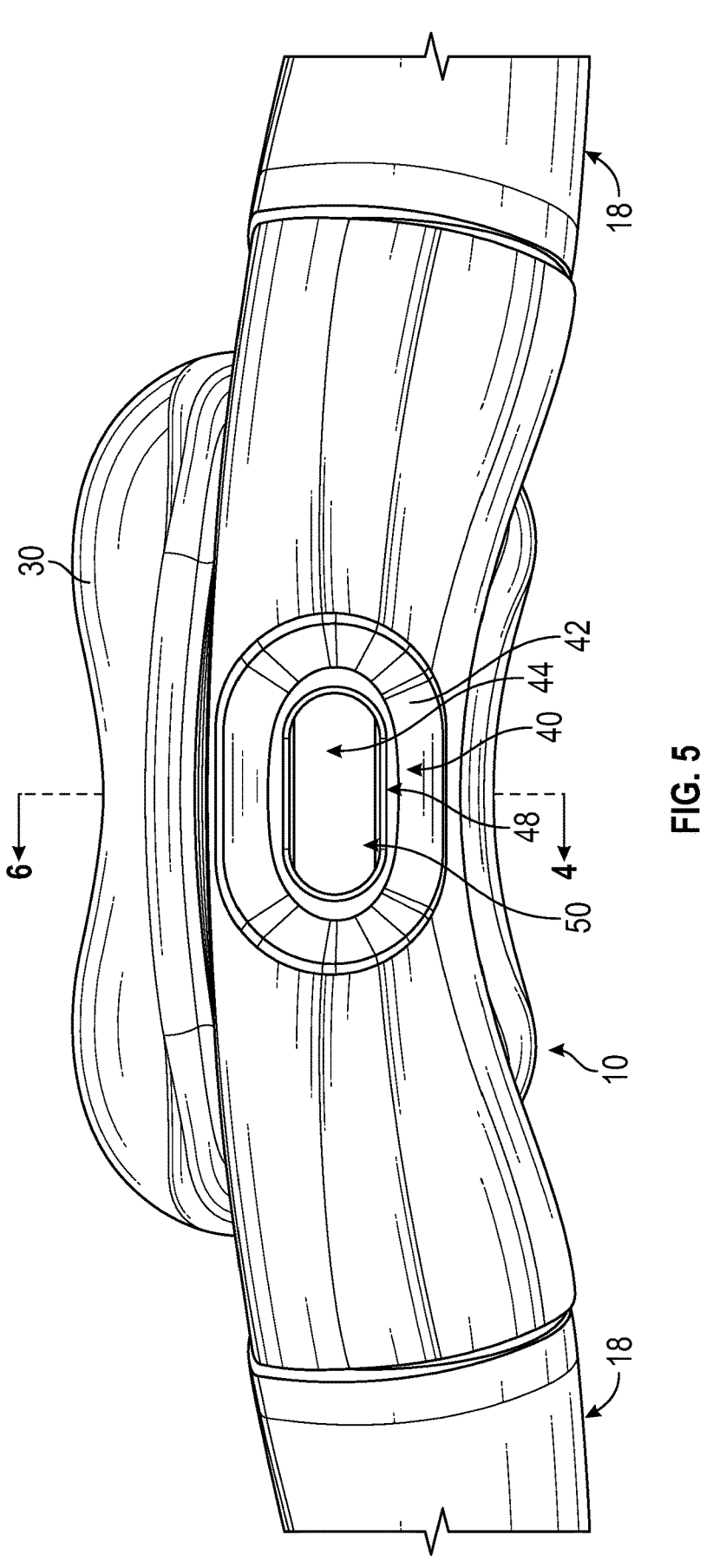
FIG. 5 is a detail view of the front of the patient interface of the system of FIGS. 1 and 2 shown with a diffusion element included in an exhaust arrangement thereof.
Figure 6:
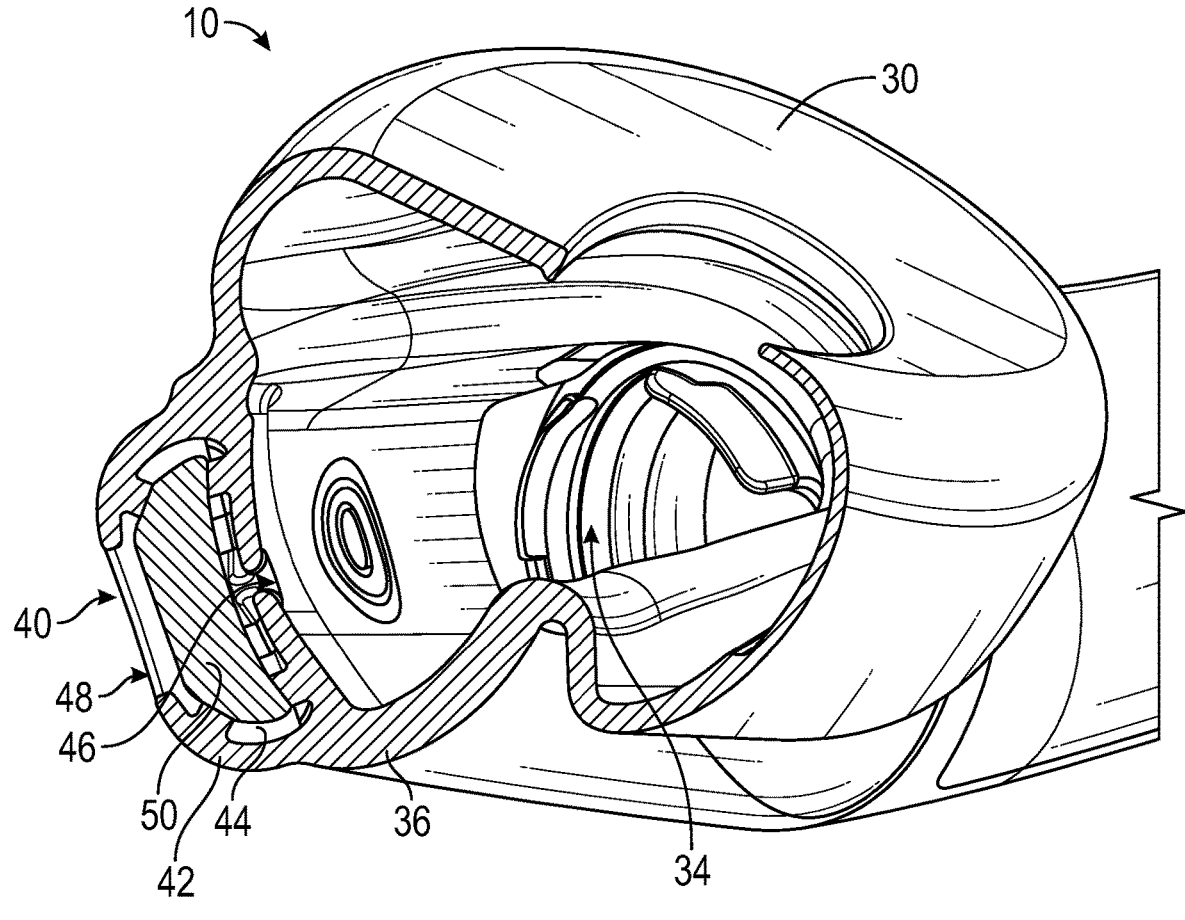
FIG. 6 is a sectional view of the patient interface of FIG. 5 taken along line 6-6 of FIG. 5.

Diffuser element 50 may be composed of a porous or other suitable material that can effectively absorb airflow, e.g., without limitation, felt, fabric(s), spacer fabric(s), foam(s), mesh(es), filter material(s), etc. In an example embodiment of the present invention such as shown in FIGS. 4 and 7A, diffuser inlet 46 and diffuser outlet 48 are coaxially aligned about a reference axis 51 with diffuser element constrained therebetween (further discussed below) such that gases passing between diffuser inlet 46 and diffuser outlet 48 do not have a direct (i.e., linear) pathway through diffuser cavity 44 that is not occupied by diffuser element 50.

Figure 7A:
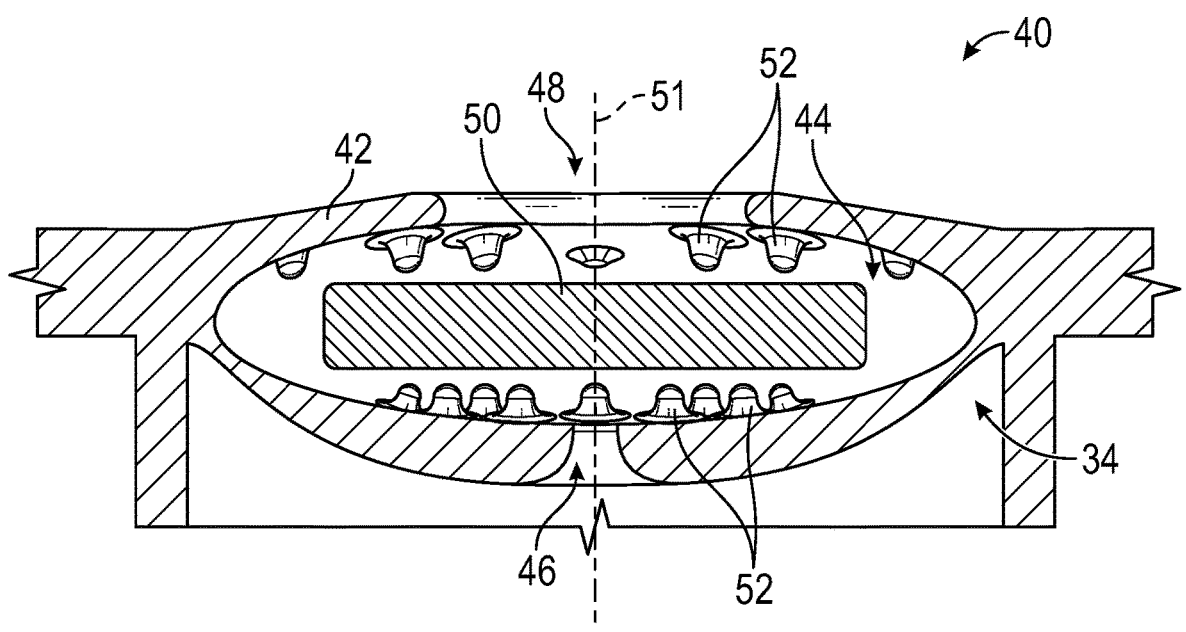
FIG. 7A is a sectional view of a portion of the patient interface of FIGS. 3 and 4 taken along line 7-7 of FIG. 3 showing the diffuser outlet in an undeformed positioning having a first sizing.
Figure 7B:
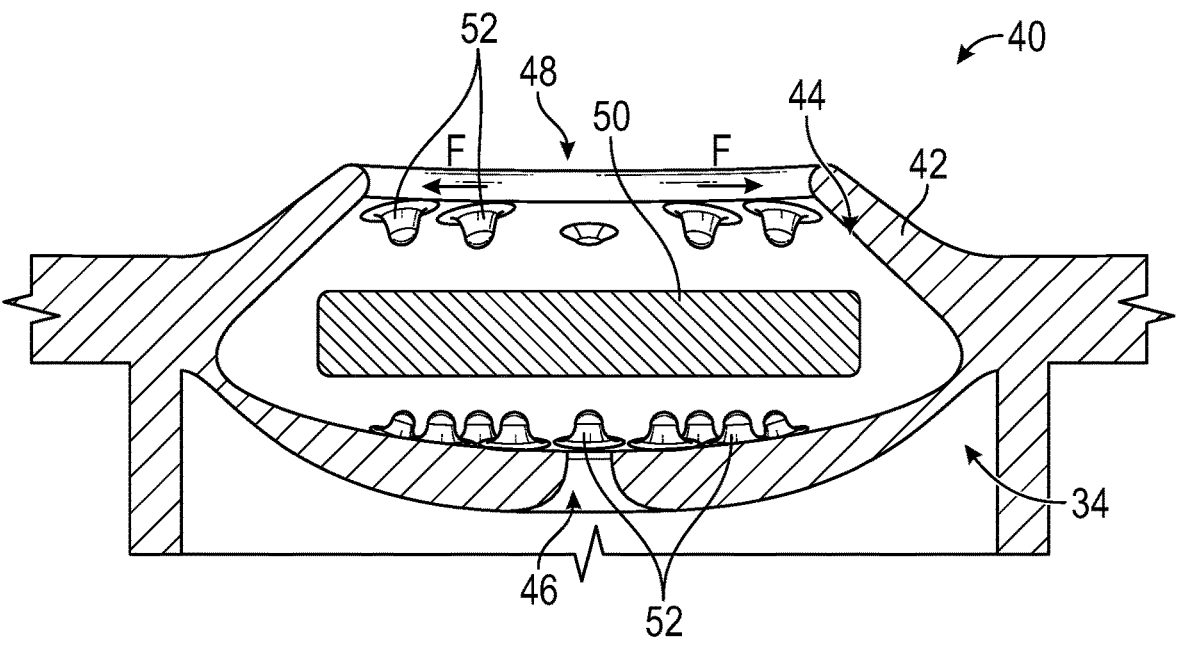
FIG. 7B is another sectional view of the portion of the patient interface of FIGS. 3 and 4 taken along line 7-7 of FIG. 3 shown in FIG. 7A except with the diffuser outlet shown in a deformed second positioning having a second sizing.

In an example embodiment such as shown in FIGS. 7A and 7B, diffuser housing is formed from an elastic material (e.g., silicone) adjacent diffuser outlet 48 such that diffuser outlet 48 is elastically deformable from a first sizing (such as shown in FIG. 7A) to a second sizing (such as shown in FIG. 7B). In the first sizing (such as shown in FIG. 7A) in which diffuser housing 42 is in a relaxed position, diffuser element 50 cannot pass through diffuser outlet 48 due to the relative sizing between such elements and thus diffuser element 50 is captively positioned within diffuser cavity 44. In the second sizing (such as shown in FIG. 7B), diffuser element 50 can readily pass through diffuser outlet 48 for placing diffuser element 50 in, or removing diffuser element 50 from, diffuser cavity 44.

Figure 8:
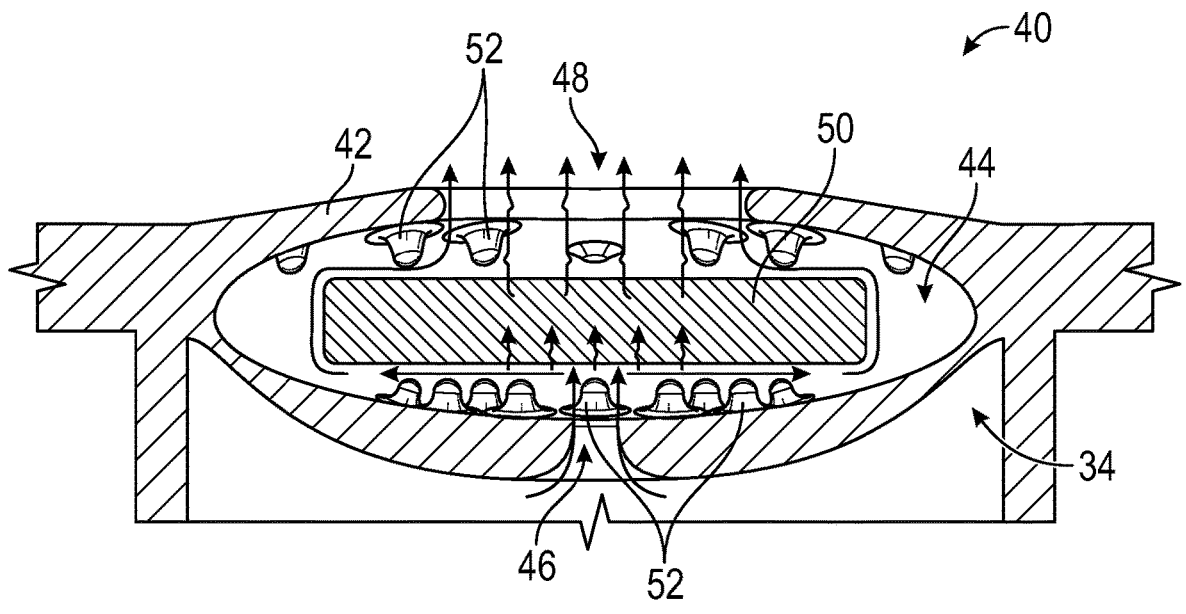
FIGS. 8 and 9 are other versions of the sectional view of FIG. 7 shown with a schematic representation of a diffusion element housed therein similar to FIGS. 5 and 6.
Figure 9:
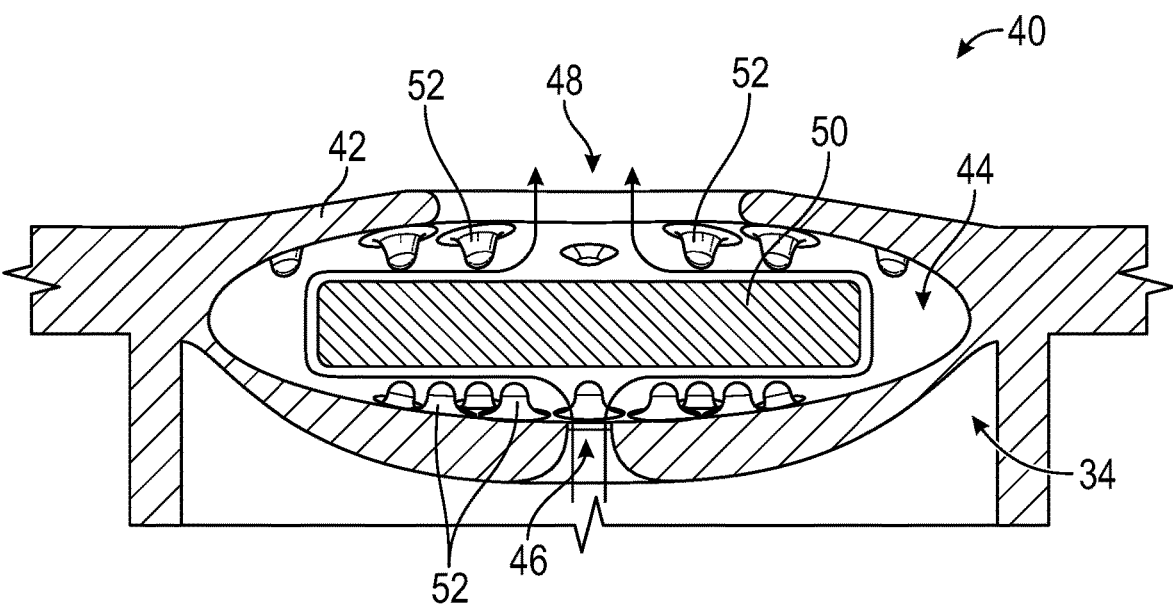
Figure 10A:
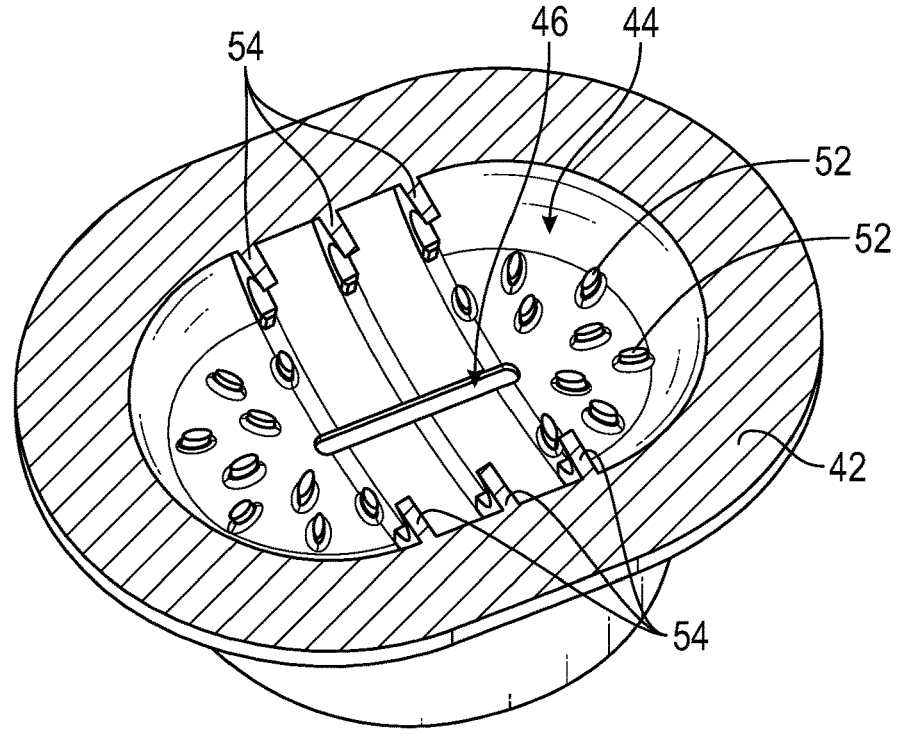
FIGS. 10A and 10B are perspective views of inner and outer portions of a portion of a patient interface in accordance with another example embodiment of the present invention.
Figure 10B:
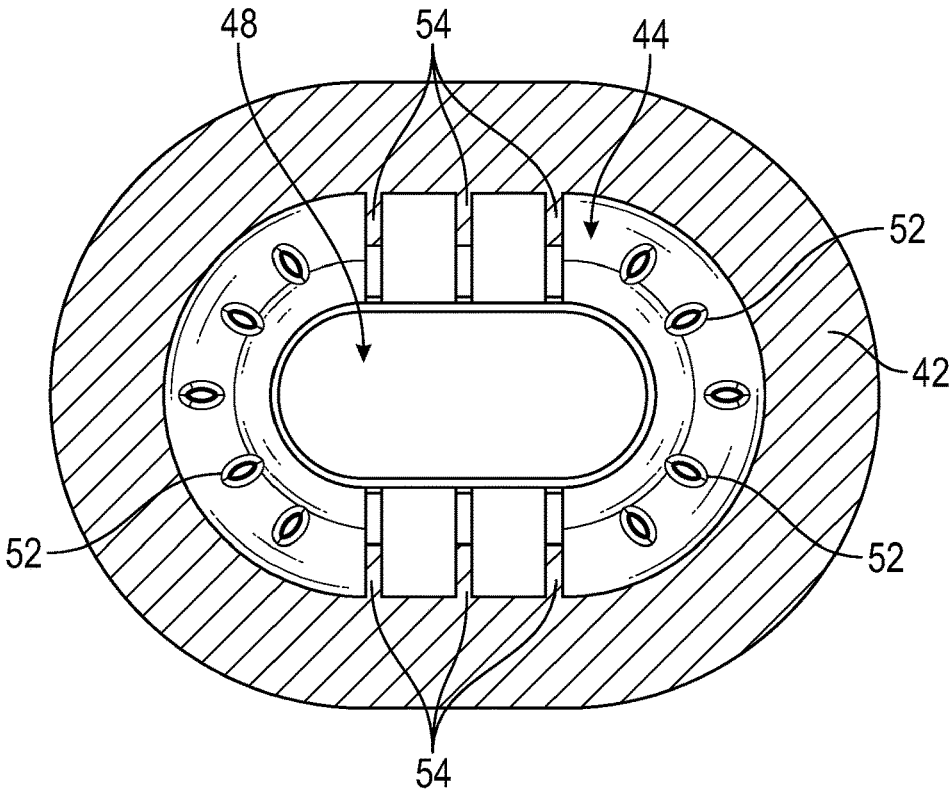

Referring to FIGS. 7A, 7B, 8 and 9, exhaust diffuser arrangement 40 further includes a number of protrusions 52 (only some of which are labeled) extending into diffuser cavity 44 from diffuser housing 42. In an example embodiment, each protrusion 52 is integrally formed as a portion of diffuser housing 42, however, one or more of protrusions 52 may be formed as a separate element without varying from the scope of the present invention. As shown in FIGS. 8 and 9, each protrusion 52 is structured to space diffuser element 50 from a corresponding portion of diffuser housing 42 to form a non-linear pathway between diffuser element 50 and diffuser housing 42 that extends from diffuser inlet 46 to diffuser outlet 48. As shown by the arrows in the view of FIG. 8, such arrangement provides for a flow of exhaust gas to pass around diffuser element 50 along a non-linear, tortuous path from diffuser inlet 46 to diffuser outlet 48, in addition to being able to pass through diffuser element 50.

As shown in FIG. 9, such arrangement also provides for a flow of exhaust gas to completely bypass diffuser element 50 in moving from diffuser inlet 46 to diffuser outlet 48 in the event that diffuser element 50 becomes saturated and/or otherwise clogged. In addition to, or instead of protrusions 52, exhaust diffuser arrangement 40 may include a number of ribs 54 extending into diffuser cavity 44 from diffuser housing 42. In an example embodiment, each rib 54 is integrally formed as a portion of diffuser housing 42, however, one or more of ribs 54 may be formed as a separate element without varying from the scope of the present invention. Each rib 54 functions in a similar manner as protrusions 52 with the additional ability to more selectively control the passage of gases from diffuser inlet 46 to diffuser outlet 48 due to their elongated shape which can be customized as needed for a particular application. It is to be appreciated that in addition to, or in place of such protrusions 52 and ribs 54, protruding elements of other shape(s) and sizing(s) may be employed without varying from the scope of the present invention.

From the foregoing it is to be appreciated that embodiments of the present invention provide means for diffusing air that is exhaled by a patient using a CPAP machine. Embodiments of the present invention further provide optimized flow paths for the air being exhaled from a patient.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. An exhaust diffuser arrangement for exhausting gases from a main cavity of a patient interface used in providing a flow of a breathing gas to the airway of a patient, the exhaust diffuser arrangement comprising:
   a diffuser housing;
   a diffuser cavity defined within the diffuser housing, the diffuser cavity being sized and configured to house a diffuser element therein;
   a diffuser inlet defined in the diffuser housing, the diffuser inlet structured to communicate gases from the main cavity to the diffuser cavity; and
   a diffuser outlet defined in the diffuser housing, the diffuser outlet structured to communicate gases from the diffuser cavity to an exterior environment to the patient interface,
   wherein the diffuser housing is formed from an elastic material adjacent the diffuser outlet such that the diffuser housing, and thus the diffuser outlet, is elastically deformable from:
      a first sizing wherein the diffuser outlet is structured to prohibit the diffuser element from passing therethrough and thus the diffuser element is captively positioned within the diffuser cavity; and
      a second sizing in which the diffuser outlet is structured to allow the diffuser element to readily pass through the diffuser outlet for placing the diffuser element in, or removing the diffuser element from, the diffuser cavity.

2. The exhaust diffuser arrangement of claim 1, further comprising a number of protrusions extending into the diffuser cavity from the diffuser housing, wherein each protrusion of the number of protrusions is structured to space the diffuser element from a corresponding portion of the diffuser housing to form a non-linear pathway between the diffuser element and the diffuser housing that extends from the diffuser inlet to the diffuser outlet.

3. The exhaust diffuser arrangement of claim 1, further comprising a number of ribs extending into the diffuser cavity from the diffuser housing, wherein each rib of the number of ribs is structured to space the diffuser element from a corresponding portion of the diffuser housing to form a non-linear pathway between the diffuser element and the diffuser housing that extends from the diffuser inlet to the diffuser outlet.

4. The exhaust diffuser arrangement of claim 1, further comprising the diffuser element captively positioned within the diffuser cavity.

5. The exhaust diffuser arrangement of claim 4, wherein the diffuser element comprises absorbent material.

6. A patient interface for use in providing a flow of a breathing gas to the airway of a patient, the patient interface comprising:
   a sealing arrangement structured to sealingly engage about an airway of the patient;
   a body;
   a main cavity defined within the body, the main cavity being structured to receive the flow of breathing gas;

a patient aperture surrounded by the sealing arrangement, the patient aperture structured to convey the flow of breathing gas from the main cavity to the airway of the patient; and an exhaust diffuser arrangement comprising:

a diffuser housing;

a diffuser cavity defined within the diffuser housing;

a diffuser element captively positioned within the diffuser cavity;

a diffuser inlet defined in the diffuser housing, the diffuser inlet structured to communicate gases from the main cavity to the diffuser cavity; and a diffuser outlet defined in the diffuser housing, the diffuser outlet structured to communicate gases from the diffuser cavity to an exterior environment to the patient interface, wherein the diffuser housing is formed from an elastic material adjacent the diffuser outlet such that the diffuser housing, and thus the diffuser outlet, is elastically deformable among:

a first sizing in which the diffuser element cannot pass through the diffuser outlet and thus is captively positioned within the diffuser cavity, and a second sizing in which the diffuser element can readily pass through the diffuser outlet for placing the diffuser element in, or removing the diffuser element from, the diffuser cavity.

7. The patient interface of claim 6, wherein the diffuser element comprises absorbent material.

8. The patient interface of claim 6, further comprising a number of protrusions extending into the diffuser cavity from the diffuser housing, wherein each protrusion of the number of protrusions spaces the diffuser element from a corresponding portion of the diffuser housing to form a non-linear pathway between the diffuser element and the diffuser housing that extends from the diffuser inlet to the diffuser outlet.

9. The patient interface of claim 6, further comprising a number of ribs extending into the diffuser cavity from the diffuser housing, wherein each rib of the number of ribs spaces the diffuser element from a corresponding portion of the diffuser housing to form a non-linear pathway between the diffuser element and the diffuser housing that extends from the diffuser inlet to the diffuser outlet.

10. The patient interface of claim 6, wherein the diffuser housing is integrally formed with the body of the patient interface.

11. An arrangement for providing a flow of treatment gas to the airway of a patient, the arrangement comprising:

a tubing assembly comprising a manifold portion and a number of tubular portions, each tubular portion extending from the manifold portion to a distal end, the manifold portion being structured to receive the flow of treatment gas and each tubular portion being structured to convey the flow of treatment gas from the manifold portion to the distal end thereof; and a patient interface coupled to the distal end of each tubular portion, the patient interface comprising:

a sealing arrangement structured to sealingly engage about an airway of the patient;

a body;

a main cavity defined within the body, the main cavity being structured to receive the flow of treatment gas from the distal end of each tubular portion;

a patient aperture surrounded by the sealing arrangement, the patient aperture structured to convey the flow of treatment gas from the main cavity to the airway of the patient; and an exhaust diffuser arrangement comprising:

a diffuser housing;

a diffuser cavity defined within the diffuser housing;

a diffuser element captively positioned within the diffuser cavity;

a diffuser inlet defined in the diffuser housing, the diffuser inlet structured to communicate gases from the main cavity to the diffuser cavity; and a diffuser outlet defined in the diffuser housing, the diffuser outlet structured to communicate gases from the diffuser cavity to an exterior environment to the patient interface, wherein the diffuser housing is formed from an elastic material adjacent the diffuser outlet such that the diffuser housing, and thus the diffuser outlet, is elastically deformable among:

a first sizing in which the diffuser element cannot pass through the diffuser outlet and thus is captively positioned within the diffuser cavity, and a second sizing in which the diffuser element can readily pass through the diffuser outlet for placing the diffuser element in, or removing the diffuser element from, the diffuser cavity.

12. The arrangement of claim 11, wherein the diffuser element comprises absorbent material.

13. The arrangement of claim 11, further comprising a number of protrusions extending into the diffuser cavity from the diffuser housing, wherein each protrusion of the number of protrusions spaces the diffuser element from a corresponding portion of the diffuser housing to form a non-linear pathway between the diffuser element and the diffuser housing that extends from the diffuser inlet to the diffuser outlet.

14. The arrangement of claim 11, further comprising a number of ribs extending into the diffuser cavity from the diffuser housing, wherein each rib of the number of ribs spaces the diffuser element from a corresponding portion of the diffuser housing to form a non-linear pathway between the diffuser element and the diffuser housing that extends from the diffuser inlet to the diffuser outlet.

15. The arrangement of claim 11, wherein the diffuser housing is integrally formed with the body of the patient interface.

* * * * *